United States Patent
Pavia

(10) Patent No.: US 10,319,560 B2
(45) Date of Patent: Jun. 11, 2019

(54) METHOD OF DETERMINING CRYSTALLOGRAPHIC PROPERTIES OF A SAMPLE AND ELECTRON BEAM MICROSCOPE FOR PERFORMING THE METHOD

(71) Applicant: Carl Zeiss Microscopy GmbH, Jena (DE)

(72) Inventor: Giuseppe Pavia, Aalen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 15/209,988

(22) Filed: Jul. 14, 2016

(65) Prior Publication Data

US 2017/0025249 A1    Jan. 26, 2017

(30) Foreign Application Priority Data

Jul. 23, 2015   (EP) .................................... 15002188

(51) Int. Cl.
*H01J 37/06*    (2006.01)
*H01J 37/244*   (2006.01)
*G01N 23/2251*  (2018.01)

(52) U.S. Cl.
CPC ........ *H01J 37/244* (2013.01); *G01N 23/2251* (2013.01); *H01J 37/06* (2013.01);
(Continued)

(58) Field of Classification Search
None
See application file for complete search history.

(56) References Cited

U.S. PATENT DOCUMENTS

| 6,066,849 A * | 5/2000 | Masnaghetti ........... H01J 37/28 250/310 |
| 2004/0061053 A1 * | 4/2004 | Taniguchi ............... G01L 1/241 250/310 |

(Continued)

OTHER PUBLICATIONS

P. W. Trimby, "Orientation mapping of nano structured materials using transmission Kikuchi diffraction in the scanning electron microscope", Ultramicroscopy, vol. 120, 2012, pp. 16-24.*
(Continued)

*Primary Examiner* — Andrew Smyth
(74) *Attorney, Agent, or Firm* — Fish & Richardson P.C.

(57) ABSTRACT

A method of determining crystallographic properties of a sample includes: generating first and second electron beams of electrons having first and second mean kinetic energies, respectively; detecting, for each of first locations of a region of the sample, a two-dimensional spatial distribution of electrons incident onto a detection area while directing the first electron beam onto the first locations; generating, for each of the first locations, first data representing the two-dimensional spatial distribution; detecting, for each of second locations of the region of the sample, a two-dimensional spatial distribution of electrons incident onto the detection area while directing the second electron beam onto the second locations; generating, for each of the second locations, second data representing the two-dimensional spatial distribution; and determining the crystallographic properties for target locations of the region based on the first data of the first locations and the second data of the second locations.

22 Claims, 7 Drawing Sheets

(52) U.S. Cl.
CPC ............... *G01N 2223/633* (2013.01); *H01J 2237/24585* (2013.01)

(56) References Cited

U.S. PATENT DOCUMENTS

| | | | | |
|---|---|---|---|---|
| 2005/0061974 A1* | 3/2005 | Kim | G01N 23/04 | 250/310 |
| 2009/0206254 A1* | 8/2009 | Takahashi | G01N 1/286 | 250/307 |
| 2011/0266440 A1* | 11/2011 | Boughorbel | H01J 37/222 | 250/310 |
| 2015/0214004 A1* | 7/2015 | Pavia | H01J 37/28 | 250/307 |

OTHER PUBLICATIONS

Trimby, ("Orientation mapping of nano structured materials using transmission Kikuchi diffraction in the scanning electron microscope", Ultramicroscopy, vol. 120, 2012, pp. 16-24).*

R.R. Keller et al., "Transmission EBSD from 10 nm domains in a scanning electron microscope", Journal of Microscopy, vol. 245, Pt. 3, 2012, pp. 245-251.

L. Reimer, "Scanning Electron Microscopy: Physics of Image Formation and Microanalysis", Springer, Chapter 9, 1998, pp. 329-377.

Oxford Instruments, "Improving the spatial resolution of EBSD using transmission Kikuchi diffraction in the SEM", Application Note, 2013, pp. 1-4.

R. Keller et al., "Transmission Kikuchi Diffraction in the Scanning Electron Microscope", Bruker Webinar, 2013, pp. 1-36.

Extended European search report for corresponding EP application No. 15 002 188.9, dated Jan. 29, 2016.

European Office Action for corresponding Appl No. 15 002 188.9, dated Jun. 12, 2018.

Felisari Let Al: "Imaging with low-voltage scanning transmission electron microscopy: A quantitative analysis", UL Tramicroscopy, Elsevier, Amsterdam, NL, vol. 111, No. 8, Mar. 19, 2011 (Mar. 19, 2011), pp. 1018-1028, XP028268473, ISSN: 0304-3991, DOI: 10.1016/J.ULTRAMIC.2011.03.016.

\* cited by examiner

METHOD OF DETERMINING CRYSTALLOGRAPHIC PROPERTIES OF A SAMPLE AND ELECTRON BEAM MICROSCOPE FOR PERFORMING THE METHOD

CROSS-REFERENCE TO RELATED APPLICATIONS

This application claims benefit under 35 U.S.C. § 119 to European Application No. 15 002 188.9, filed Jul. 23, 2015. The content of this applications is hereby incorporated by reference in its entirety.

FIELD

The disclosure relates to a method of determining crystallographic properties of a sample and to an electron beam microscope configured to perform the method. In particular, the method relates to determining crystallographic properties of a sample by analyzing electron diffraction patterns of the sample wherein the electron diffraction patterns comprise Kikuchi bands.

BACKGROUND

A conventional method of determining crystallographic properties such as an orientation of a lattice structure at plural locations of a sample comprises generating an electron beam having electrons of a given mean kinetic energy and a given kinetic energy range, directing the electron beam to the plural locations of the sample, detecting an electron diffraction pattern for each of the locations, analyzing the electron diffraction patterns comprising Kikuchi bands, and determining the crystallographic properties for the plural locations based on the analyzed electron diffraction patterns. The kinetic energy range may be sufficiently small so that electron diffraction patterns may be obtained. Accordingly, for each of the locations, an electron diffraction pattern is detected and analyzed and the crystallographic properties are determined based on the analyzed diffraction pattern.

When detecting the diffraction pattern in transmission, i.e. on a side of the sample opposite to a side onto which the electron beam is incident, the sample must be sufficiently thin. Otherwise, if the sample is not sufficiently thin, the diffraction pattern may show insufficient contrast and, accordingly, may not yield proper results.

Furthermore, if the sample is not sufficiently thin, the diffraction pattern may comprise Kikuchi bands originating from multiple different sections of the sample disposed along the direction of the electron beam resulting in a superposition of plural individual diffraction patterns of each section. In this case, the diffraction pattern may indicate plural different crystallographic properties.

Another problem arises even for sufficiently thin samples, if the sample is of inhomogeneous thickness in a region, the crystallographic properties of which are to be determined. The kinetic energy of the electrons of the electron beam incident onto the region of inhomogeneous thickness may be selected as to provide diffraction patterns of good quality for a first thickness of the sample within the region. However, the diffraction pattern originating from locations where the sample has a thickness different from the first thickness are usually blurred and suffer from too little scattering power or too large absorption of the sample. Accordingly, a problem of conventional methods is that the crystallographic properties of a sample of inhomogeneous thickness cannot be properly determined.

SUMMARY

The present invention seeks to provide a method of determining crystallographic properties of a sample, in particular a sample having an inhomogeneous thickness, which allows to determine the crystallographic properties better. The present disclosure also seeks to provide an apparatus configured to perform the method.

An embodiment of a method of determining crystallographic properties of a sample comprises generating a first electron beam of electrons having a first mean kinetic energy; detecting, for each of first locations of a region of the sample, a two-dimensional spatial distribution of electrons emerging from the sample and being incident onto a detection area while directing the first electron beam onto the first locations; generating, for each of the first locations, first data representing the two-dimensional spatial distribution; generating a second electron beam of electrons having a second mean kinetic energy different from the first mean kinetic energy; detecting, for each of second locations of the region of the sample, a two-dimensional spatial distribution of electrons emerging from the sample and being incident onto the detection area while directing the second electron beam onto the second locations; generating, for each of the second locations, second data representing the two-dimensional spatial distribution; and determining the crystallographic properties for target locations of the region based on the first data of the first locations and the second data of the second locations.

The crystallographic properties determined by the method may be at least one of an orientation of a lattice structure, a lattice type and lattice parameters. The lattice structure may be the structure of the lattice representing an arrangement of the individual atoms in the vicinity of a location of the sample. The orientation of the lattice structure may be the three dimensional orientation of the lattice structure with respect to a reference coordinate system such as a local coordinate system of the sample or a coordinate system of an electron beam microscope performing the method. The lattice type may be one of the Bravais lattices such as a triclinic, monoclinic or tetragonal lattice. The lattice parameters comprise lengths of the primitive vectors of the lattice and the angles in between the primitive vectors.

The method comprises generating a first electron beam of electrons having a first mean kinetic energy. Herein, the mean kinetic energy is an energy value representing an average of a distribution of kinetic energies of electrons of the electron beam. The method further comprises generating a second electron beam of electrons having a second mean kinetic energy different from the first mean kinetic energy. Accordingly, the first and second electron beams differ with respect to the mean kinetic energy of their electrons. In particular, the first and second mean kinetic energies differ by at least one of 1 keV, 2 keV, 5 keV and 10 keV, and 1%, 2%, 5% and 10% of a mean value of the first mean kinetic energy and the second mean kinetic energy. Furthermore, the first and second mean kinetic energies may be energy values in a range of 10 keV to 30 keV, in particular 15 keV to 25 keV.

While the first electron beam is directed onto a region of the sample containing first locations, a two-dimensional spatial distribution of electrons emerging from the sample and being incident onto a detection area is detected for each of the first locations. The electrons emerging from the sample may be electrons of the first electron beam being diffracted in the vicinity of the first location and being incident onto a detection area of an electron detector such as a CCD detector (charge-coupled device). In particular, the electrons incident onto the detection area may be transmitted through the sample. The two-dimensional spatial distribution of these diffracted electrons represents a diffraction pattern associated with the particular first location, the first electron beam is currently directed to. In particular, the two-dimensional spatial distribution represents a diffraction pattern comprising Kikuchi bands.

Subsequently, for each of the first locations contained in the region, first data representing the two-dimensional spatial distribution of electrons is generated. Accordingly, the number of the first data is equal to the number of the first locations.

As each of the first data of the first locations represents a two-dimensional spatial distribution of electrons, the crystallographic properties of the sample at each of the first locations can be determined.

While the second electron beam is directed onto second locations, wherein the second locations are also contained in the region containing the first locations, a two-dimensional spatial distribution of electrons emerging from the sample and being incident onto the detection area is detected for each of the second locations. Also each of the two-dimensional spatial distributions detected for a particular second location represents a diffraction pattern associated with the particular second location.

For each of the second locations, second data is generated representing the two-dimensional spatial distribution detected while directing the second electron beam onto the second locations. Accordingly, the number of the second data is equal to the number of the second locations. As each of the second data represents a two-dimensional spatial distribution representing a diffraction pattern originating from the second location associated with the second data. The crystallographic properties for each of the second locations may be determined based on the second data of the second locations.

As the first and second locations are contained in the same region of the sample, the crystallographic properties of the same region may be determined based on plural data sets, namely the first data of the first locations and the second data of the second locations.

The method further comprises determining the crystallographic properties for target locations of the region based on the first data of the first locations and the second data of the second locations. The target locations are locations of the sample, the crystallographic properties of which are to be determined. The first and second locations may coincide with the locations represented by the target locations. However, in practice, the first and second locations may be located in close proximity to the target locations.

As the target locations define the locations of the sample for which the crystallographic properties are to be determined, the target locations may define the region containing the first and second locations. In particular, the region may be regarded as a convex hull of the target locations. A convex hull of the target locations is the smallest convex set (of locations) containing the target locations. More in particular, the region may be defined by a boundary containing the convex hull of the target locations, wherein a shortest distance from a point on the boundary to the convex hull is less than a predetermined value, e. g. 5 nm, 50 nm or 500 nm. Similarly, the region may be defined by a boundary containing the convex hull of the target locations, wherein a distance from a point on the boundary to the target location closest to the point is less than the predetermined value above.

Therefore, the target locations may define the region, the crystallographic properties of which are determined. The target locations may be distributed in the sample, for example, as a regular array.

According to an embodiment, the method may further comprise generating a third electron beam of electrons having a third mean kinetic energy; detecting, for each of third locations of the region, a two-dimensional spatial distribution of electrons emerging from the sample and being incident onto the detection area while directing the third electron beam onto the third locations; generating, for each of the third locations, third data representing the two-dimensional spatial distribution; and determining the crystallographic properties for the target locations based on the first data of the first locations, the second data of the second locations, and the third data of the third locations.

In this embodiment the first, second and third locations are contained in the region defined by the target locations. The third mean kinetic energy may differ from both the first and second mean kinetic energies in a similar way the first and the second mean kinetic energies differ.

While three sets of locations and three mean kinetic energies were used to determine the crystallographic properties of the region of the sample in the embodiment described above, the number of sets of locations and mean kinetic energies may also amount to values greater than three. Accordingly, the determining of the crystallographic properties of the target locations may be based on a plurality of data sets, each of which is determined for a set of locations using different electron beams of electrons having different mean kinetic energies.

Next, exemplary embodiments are described. Although the features of the exemplary embodiments are described referring to the embodiment of the method using two sets of locations and mean kinetic energies only, the exemplary embodiments described below may be adapted to conform to embodiments using more than two sets of locations and mean kinetic energies.

According to an exemplary embodiment, the determining of the crystallographic properties for each current target location of a set of the target locations comprises selecting, as selected data, one of the first data of a first location associated with the current target location and the second data of a second location associated with the current target location; and determining the crystallographic properties for the current target location based on the selected data.

In this embodiment, the set of the target locations comprises at least one of the target locations. For each current target location, i.e. for each member of the set of the target locations, the selecting of the selected data and the determining of the crystallographic properties are performed. According to this embodiment, either the first data of a location associated with the current target location or the second data of a second location associated with the current target location is selected as the selected data based on which the crystallographic properties for the current target location are determined.

The first location associated with the current target location may be determined by selecting, among the first locations, in particular among the first locations contained in a region defined by the set of the target locations, the first location having a shortest distance to the current target location. Similarly, the second location associated with the current target location may be determined by selecting, among the second locations, in particular among the second locations contained in the region defined by the set of the target locations, the second location having a shortest distance to the current target location. In addition or alternatively, a first location may be associated with a current target location if a distance between the first location and the current target location is less than a predetermined value, for example 30 nm, 20 nm, 10 nm, 5 nm, 3 nm or 1 nm. Similarly, a second location may be associated with a current target location if a distance between the second location and the current target location is less than the predetermined value above.

As the selected data is one of the first and second data, the selected data also represents a two-dimensional spatial distribution of electrons based on which the crystallographic properties for the current target location are determined.

According to an exemplary embodiment herein, the selecting comprises determining a quality parameter such as a contrast value for each of the first data of the first location associated with the current target location and the second data of the second location associated with the current target location; and selecting, as the selected data, the data having the better quality parameter such as the better contrast. In this embodiment a quality parameter is determined for the first data of the first location associated with the current target location and quality parameter is determined for the second data of the second location associated with the current target location. The quality parameter may be a parameter suitable to interpret the quality of the first and second data, for example a contrast, a signal to noise ratio, a rate of identifying of Kikuchi bands, a rate of indexing of Kikuchi bands, a reliability value representing a correlation or the like between measured electron diffraction patterns comprising Kikuchi bands and simulated electron diffraction patterns, the number of Kikuchi bands identified and/or indexed and parameters suitable for discriminating sections on the detection area onto which diffracted electrons were incident from sections of the detection area where no to little numbers of diffracted electrons were incident. Multiple different quality parameters may be determined and used to select the selected data. In particular, multiple different quality parameters may be determined and used as an input to a function and/or relation yielding a value used for the selecting.

According to an exemplary embodiment, the determining of the crystallographic properties for each current target location of a set of the target locations comprises combining first data of a first location associated with the current target location and second data of a second location associated with the current target location into combined data; and determining the crystallographic properties for the current target location based on the combined data. Similar to the first and second data, the combined data may represent a two-dimensional spatial distribution of diffracted electrons. At least one quality parameter, e.g. of the quality parameters indicated above, may be determined and used for the combining and/or the determining of the crystallographic properties for the current target location.

In contrast to the previously described embodiment according to which one of the first and second data is selected to form the basis for the determining of the crystallographic properties for a current target location, in this embodiment, the first data and the second data of the first and second locations associated with the current target location are combined to form the basis for determining the crystallographic properties for the current target location.

Instead of combining the first data of a single first location and the second data of a single second location, each associated with the current target location, also the first data of a set of first locations associated with the current target location and the second data of a set of second locations associated with the current target location may be combined into the combined data. Herein, the set of locations associated with the current target location may be determined by selecting first and second locations, respectively, having a distance to the current target location being less than a predetermined value, for example 5 nm, 10 nm, 15 nm, 20 nm or 50 nm.

According to an exemplary embodiment herein, the combining comprises at least one of interpolating the first data of the first location associated with the current target location and the second data of the second location associated with current target location; and averaging the first data of the first location associated with the current target location and the second data of the second location associated with the current target location. When using first data of a set of first locations associated with the current target location and second data of a set of second locations associated with the current target location, the combining may comprise interpolating and/or averaging the first data of the set of first locations associated with the current target location and interpolating and/or averaging the second data of the set of second locations associated with the current target location. In particular, the interpolating and/or averaging may comprise assigning a weight to each of the contributing data using a parameter representing, for example, the distance of the location to the current target location or a quality parameter previously described.

According to an exemplary embodiment, the determining of the crystallographic properties for each current target location of a set of the target locations comprises determining the crystallographic properties for a first location associated with the current target location based on the first data, determining the crystallographic properties for a second location associated with the current target location based on the second data and selecting as the crystallographic properties for the current target location, one of the crystallographic properties determined for the first and second locations associated with the current target location. In this embodiment, the crystallographic properties for each of a first and second location associated with the current target location are determined and one of them is selected as the crystallographic properties for the current target location.

According to an exemplary embodiment herein, the selecting comprises determining a quality parameter, in particular a deviation from a predetermined expectation value, for each of the crystallographic properties determined for the first and second locations associated with the current target location; and selecting as the crystallographic properties of the current target location, the crystallographic properties having the better quality parameter, in particular the smaller deviation from the predetermined expectation value. In this embodiment, the predetermined expectation value is a predetermined value representing crystallographic properties.

As in the case of the previously described ways for determining the crystallographic properties for each current target location, the set of the target locations may comprise at least one of the target locations. Accordingly, plural of these ways may be employed in the method side by side for mutually exclusive sets of the target locations. Alternatively, the crystallographic properties of all target locations may be determined according to the same way.

According to an exemplary embodiment, the determining of the crystallographic properties comprises identifying and indexing of Kikuchi bands. Herein, Kikuchi bands are identified in the two-dimensional spatial representations of electrons by Hough-transforming the two-dimensional spatial distributions of electrons and analyzing the transformed data. The indexing may comprise comparing identified features to predetermined expected features.

According to an exemplary embodiment, the detecting of the two-dimensional spatial distributions of electrons comprises generating detection signals representing the two-dimensional distributions of intensities of electrons incident onto the detection area. In particular, the detected electrons may be electrons transmitted through the sample.

According to an exemplary embodiment, the method further comprises generating an image representation of the crystallographic properties of the target locations. For example, the crystallographic properties of the sample, in particular the region defined by the target locations, may be arranged in an image representing the crystallographic properties in dependence of the target locations, i.e. as a two-dimensional image of the crystallographic properties.

According to an exemplary embodiment, the method further comprises recording a first image of the sample when using the first electron beam, recording a second image of the sample when using the second electron beam; and aligning the first and second locations based on the first and second images. The first and second images may be a secondary electron image determined in transmission or reflection. In particular, the first and second images contain the region defined by the target locations. The aligning of the first and second locations based on the first and second images may comprise adjusting at least one component of an electron beam microscope generating the electron beams, for example a deflector, a stigmator, a stage to which the sample is mounted and control signals controlling these components. The aligning may be automated or manually performed and a marker may be disposed on the sample for facilitating the aligning.

According to an exemplary embodiment, the generating of the first and second electron beams comprises selecting the first and second mean kinetic energies based on sample information, in particular a thickness profile of the sample. Alternatively or in addition, the first and second mean kinetic energies may be selected based on two-dimensional spatial distributions of electrons emerging from the sample and being incident onto the detection area, in particular a quality parameter associated with the two-dimensional spatial distributions. Therefore, the mean kinetic energies of the electron beams can be selected so that the electron diffraction patterns generated at sections of the sample having different thicknesses are yet of good quality.

According to an exemplary embodiment, the method further comprises determining the first and second locations based on sample information, in particular a thickness profile of the sample. Therefore, detecting of the two-dimensional spatial distributions of electrons at locations for which the mean kinetic energy of the electron beam is not suitable can be avoided. Accordingly, an electron beam of electrons having a given mean kinetic energy selected in accordance with a given thickness of the sample may be directed to those locations of the sample having the given thickness. Therefore, the method may be performed faster compared to a method directing an electron beam of electrons having a given mean kinetic energy to all locations where the sample is inhomogeneous in thickness.

According to an exemplary embodiment, the directing of the first electron beam onto the first locations and the directing of the second electron beam onto the second locations comprises deflecting the first and second electron beams and/or displacing the sample relative to the first and second electron beams.

According to an exemplary embodiment, the first and second electron beams are focused to the first and second locations, respectively.

An exemplary embodiment comprises an electron beam microscope configured to perform the method of determining crystallographic properties of a sample. In particular, the electron beam microscope comprises an electron beam column, a two-dimensional spatially resolving electron detector and a controller configured to control the electron beam column and the detector and to perform the method described above.

BRIEF DESCRIPTION OF THE DRAWINGS

The foregoing as well as other advantageous features of the invention will be more apparent from the following detailed description of preferred embodiments of the invention with reference to the accompanying drawings.

DETAILED DESCRIPTION

Figure 1:
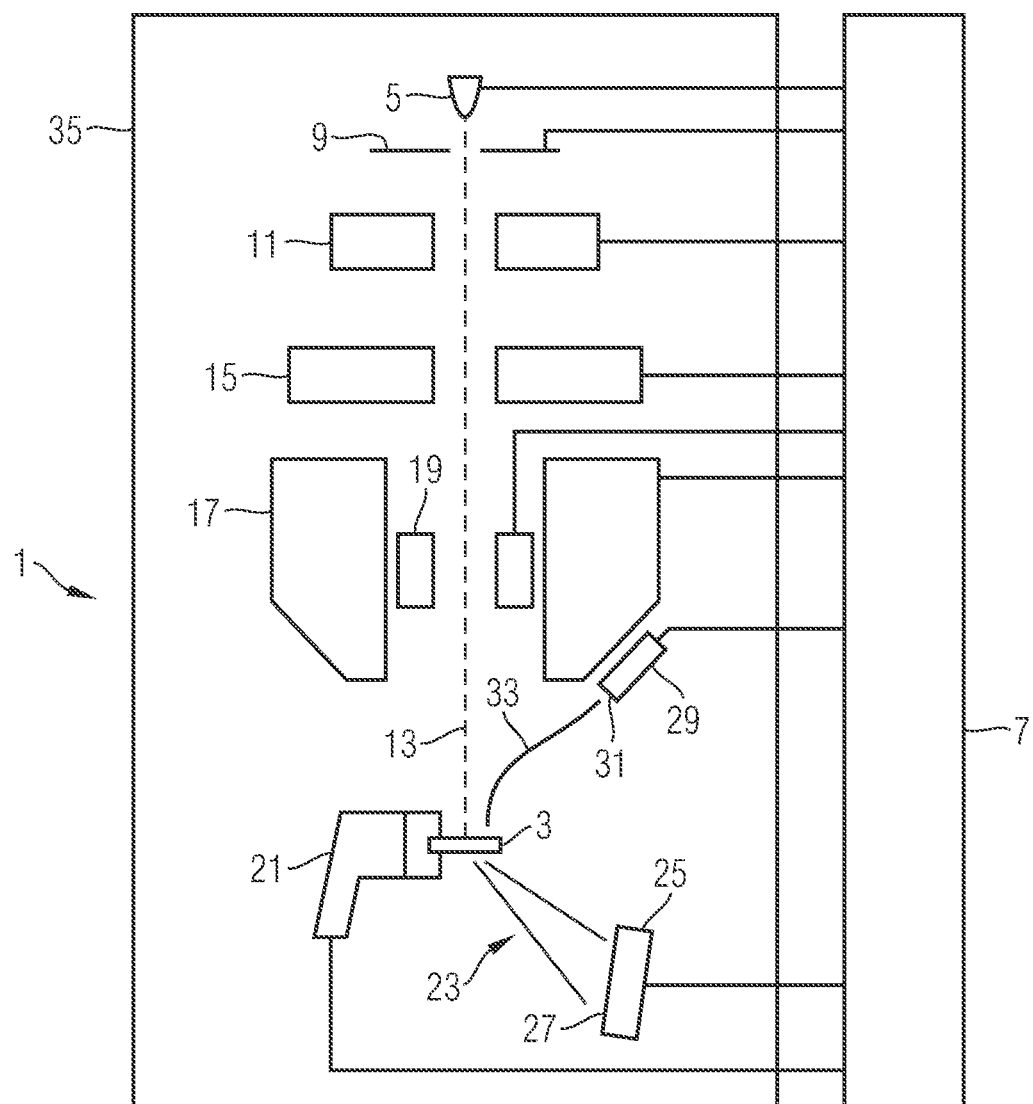
FIG. 1 shows a schematic illustration of an electron beam microscope configured to perform a method of determining crystallographic properties of a sample.

FIG. 1 shows a schematic illustration of an electron beam microscope 1 configured to perform a method of determining crystallographic properties of a sample 3. The electron microscope 1 comprises an electron source 5 configured to emit electrons according to a control signal provided to the electron source 5 by a controller 7. Further, the electron beam microscope 1 comprises an electrode 9 for accelerating the electrons emitted by the electron source 5 according to a potential generated according to a control signal provided by the controller 7. The electrons accelerated by the electrode 9 enter a condenser 11 configured to form an electron beam 13 from the electrons entering the condenser 11 and is controlled by the controller 7. The electron beam 13 next enters a stigmator 15 configured to compensate imaging errors of an objective lens 17 configured to focus the electron beam 13 onto the sample 3. The stigmator 15 and the objective lens 17 are controlled by the controller 7. The electron beam microscope 1 further comprises a deflector 19 configured to deflect the electron beam to locations of the sample according to a control signal provided to the deflector 19 by the controller 7. The sample 3 is mounted to a sample mount 21 configured to hold the sample 3 and to position the sample 3 with respect to translational and rotational directions. In particular, the sample is positioned so that the electron beam 13 is incident onto a surface 40 of the sample 3 in a direction essentially orthogonal to the surface 40. However, the sample may also be positioned so that the electron beam 13 is incident onto the surface 40 of the sample 3 in a direction tilted relative to the surface 40. For example, an angle between the electron beam 13 and a normal of the surface 40 may amount to approximately 10°, 20° or 30°. Having interacted with the sample 3, the electron beam 13 is diffracted into plural spatial directions. A portion of the diffracted electron beam 23 is incident onto an electron detector 25 configured to detect an intensity of electrons incident onto a detection area 27 of the electron detector 25. The electron detector 25 is a spatially resolving electron detector configured to generate detection signals representing a two-dimensional spatial distribution of the intensity of the electrons incident onto the detection area 27. The electron detector 25 transmits the detection signals to the controller 7 configured to generate data representing the two-dimensional spatial distribution represented by the detection signals. The electron detector 25 is disposed on a side of the sample 3 opposite to the side onto which the electron beam 13 is incident onto. Therefore, the electron detector 25 detects diffracted electrons transmitted through the sample 3.

Furthermore, the electron beam microscope 1 comprises a secondary electron detector 29 configured to detect intensities of electrons emitted by the sample 3. In particular, the secondary electron detector 29 is configured to detect secondary electrons emitted from the sample 3 upon irradiation of the sample 3 by the electron beam 13. The secondary electron detector 29 provides a detection signal representing an intensity of electrons incident onto a detection area 31 of the secondary electron detector 29 to the controller 7 further configured to generate an image of the sample. Secondary electrons emitted from the sample 3 and being incident onto the detection area 31 are illustrated by numeral 33. Instead of or in addition to the secondary electron detector 26, a backscattered electron detector may be used.

The constituents of the electron microscope 1 are disposed in at least one vacuum chamber 35. The controller 7 may be a control system comprising plural driver circuits and a computation device such as a computer and only some or even none of the components of the controller 7 may be disposed in the at least one vacuum chamber 35.

Figure 2:
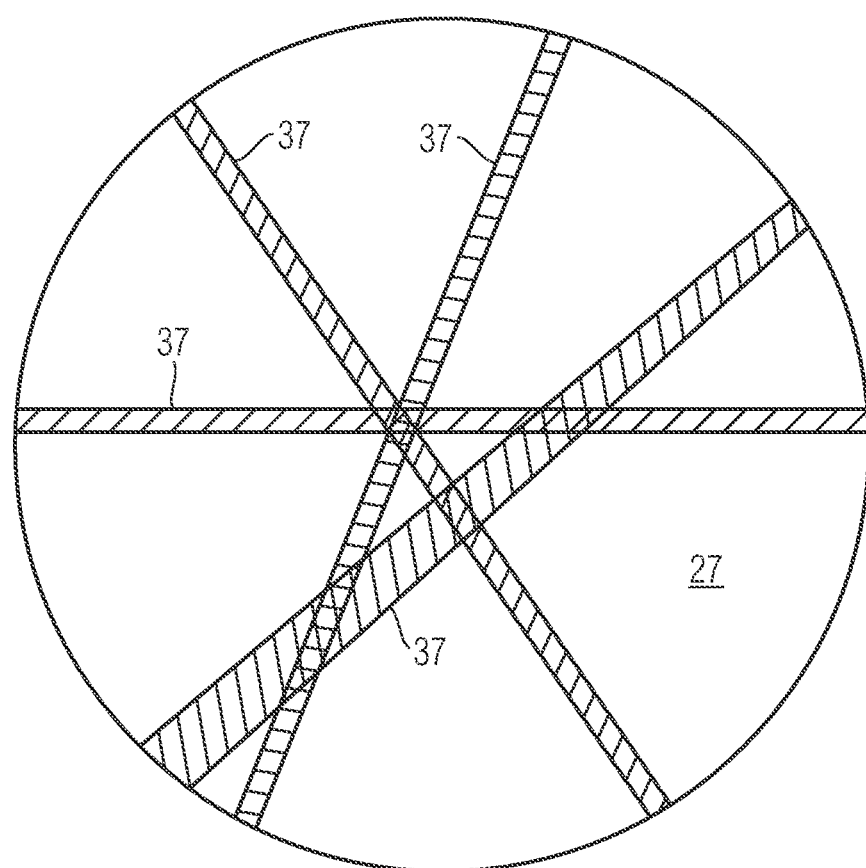
FIG. 2 shows a schematic illustration of a two-dimensional spatial distribution of electrons.

FIG. 2 shows a schematic illustration of a two-dimensional spatial distribution of the diffracted electrons 23 incident onto the detection area 27 of the electron detector 25. A diffraction pattern typical for Kikuchi diffraction comprises plural band-shaped areas 37 on the detection area 27 where the intensity of electrons incident onto the detection area 27 is high compared to other areas of the detection area 27. Although not illustrated in FIG. 2, the diffraction pattern may also comprise annular areas where the intensity of electrons incident onto the detection area 27 is high. The band-shaped and annular-shaped areas of high intensity are directly associated with a particular lattice type, orientation of a lattice structure of the lattice type and properties of the lattice structure such as the lattice parameters. In other words, the diffraction pattern is directly associated with the crystallographic properties at the location of the sample where the electron beam is incident onto and the diffracted electrons emerge from. Therefore, the crystallographic properties of a location of the sample 3 can be determined based on the diffraction pattern represented by the two-dimensional spatial distribution of electrons illustrated by the band-shaped areas 37.

An embodiment of a method of determining crystallographic properties of a sample is next described with reference to FIGS. 3A to 5.

Figure 3A:
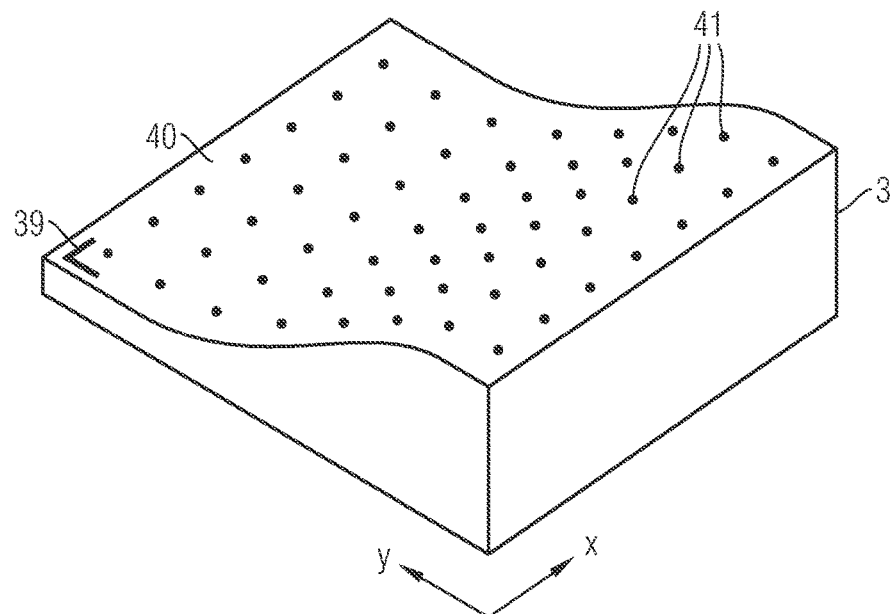
FIG. 3A shows a schematic illustration of a sample of inhomogeneous thickness.

FIG. 3A shows a schematic illustration of the sample 3 wherein the sample has an inhomogeneous thickness. The thickness of the sample 3 is changing considerably in a y-direction while the thickness is fairly constant in an x-direction. A marker 39 is provided on the surface 40 of the sample 3 onto which the electron beam 13 (shown in FIG. 1) is directed onto for facilitating handling regions of interest in practice and to illustrate geometric relations with respect to FIGS. 4A to 4E. The method allows to determine the crystallographic properties of the sample at target locations 41 indicated by dots in FIG. 3A. The target locations are distributed on the surface 40 of the sample 3 along the x- and y-directions, which correspond to long axes of the sample 3 in comparison to the thickness of the sample 3.

Figure 5:
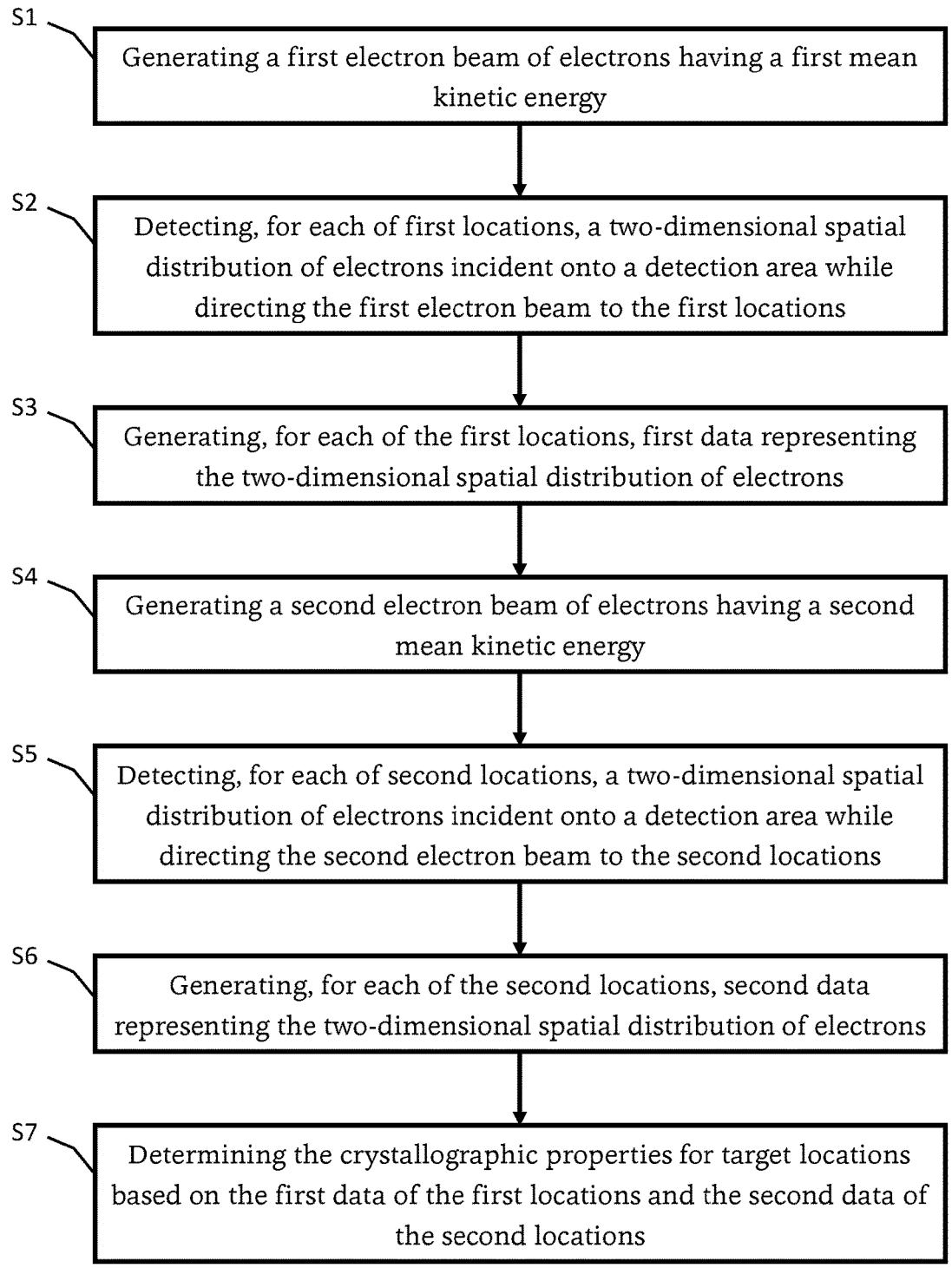
FIG. 5 shows a flowchart illustrating an embodiment of a method of determining crystallographic properties of a sample.

According to step S1 of FIG. 5, the method comprises generating a first electron beam of electrons having a first mean kinetic energy. Subsequently, according to step S2, while directing the first electron beam to first locations 43, which are illustrated as crosses in FIG. 3B, a two-dimensional spatial distribution of electrons emerging from the sample 3 and being incident onto the detection area 27 is detected for each of the first locations 43.

Figure 3B:
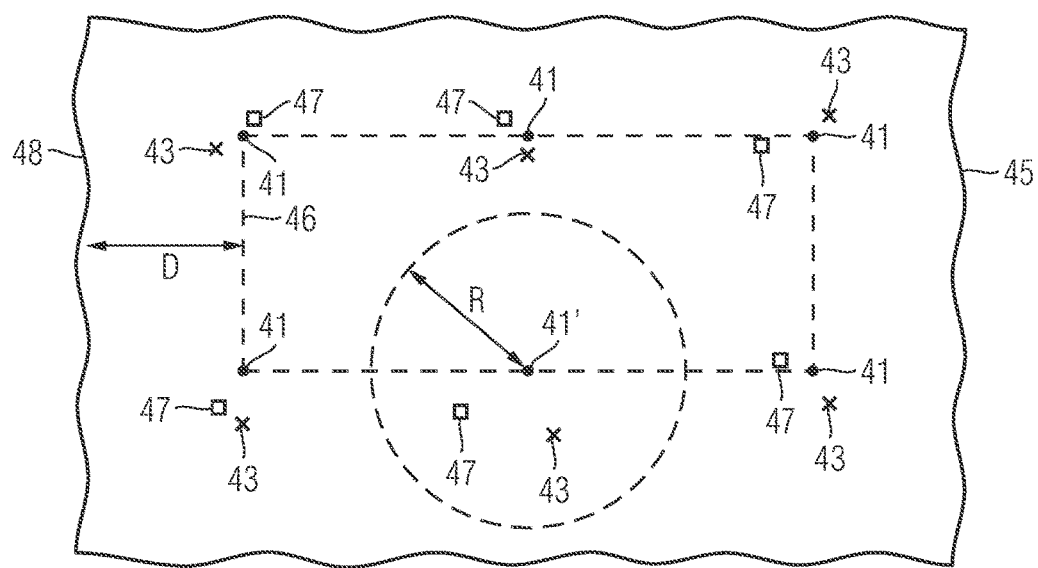
FIG. 3B shows a schematic illustration of target locations, first locations and second locations.

FIG. 3B schematically illustrates the spatial relation of the target locations 41 and the first locations 43 within a region 45 of the sample 3. A single first location 43 is in close proximity of each of the target locations 41. The small distance between a particular target location 41 and its first location 43 associated with the particular target location 41 originates from practical issues, i.e. the electron beam cannot be directed arbitrarily close to a target location due to tolerances of the electron beam microscope performing the method. However, it is possible to associate a single first location 43 to each of the target locations 41 in that the distance between a particular target location 41 to a first location 43 associated with the particular target location 41 is less than the distances of the particular target location 41 to the other first locations 43.

Therefore, according to step S2 of FIG. 5, for each of the first locations 43, a two-dimensional spatial distribution of electrons such as the one illustrated in FIG. 2 is detected while directing the first electron beam to the first locations 43.

Subsequently, in step S3, first data representing the two-dimensional spatial distribution of electrons is generated for each of the first locations 43.

Subsequently, in step S4, a second electron beam of electrons having a second mean kinetic energy different from the first mean kinetic energy is generated.

Subsequently, in step S5, while directing the second electron beam to second locations 47 of the region 45, illustrated as squares in FIG. 3B, a two-dimensional spatially distribution of electrons emerging from the sample 3 and being incident onto the detection area 27 is detected for each of the second locations 47. Similar to the description of the first locations 43, also the second locations 47 may be slightly displaced with respect to the target locations 41 due to tolerances of the electron beam microscope performing the method. However, a single second location 47 may be associated with a particular target location 41 by the condition elucidated with reference to the first locations 43.

Relations between the region 45, the target locations 41, the first locations 43, and the second locations 47 are illustrated with reference to FIG. 3B. The target locations 41, the first locations 43, and the second locations 47 may be located within the region 45 as illustrated in FIG. 3B. The region 45 may be defined by the target locations 41. For example, the region 45 may be regarded as a convex hull 46 of the target locations 41. Alternatively, the region 45 may be defined by a boundary 48 containing the convex hull 46 of the target locations 41. A distance D between a point on the boundary 48 and the convex hull or a distance between a point on the boundary 48 and a closest target location 41 may be less than a predetermined value, e. g. 5 nm, 50 nm or 500 nm.

Each of the given target locations 41 may be associated with one or more of the first locations 43. Similarly, each of the given locations 41 may be associated with one or more of the second locations 47. First and/or second locations may be regarded as to be associated with a given target location if a distance between the given target location and the first and/or second locations is less than a predetermined value, for example 30 nm, 20 nm, 10 nm, 5 nm, 3 nm or 1 nm. An exemplary distance R within which the first and/or second locations must be located about a given target location 41' in order to be regarded as to be associated with the given target location is illustrated in FIG. 3B as a circle about the given target location 41'. In the case illustrated in FIG. 3B, only a single first location and only a single second location may be regarded as to be associated with the given target location 41' as they are located within a distance R from the given target location 41'. However, in dependence of the predetermined distance R and the number of first and/or second locations per unit length or per unit area, the number of first and/or second locations associated with a given target location may be greater than one.

Note that the target locations 41, the first locations 43 and the second locations 47 are located within the region 45. In practice, the region 45 may be defined by the target locations 41.

According to step S6 of FIG. 5, second data representing the two-dimensional spatial distribution of electrons are generated for each of the second locations 47. Therefore, the second data of each of the second locations 47 represent a two-dimensional spatial distribution of electrons similar to that illustrated in FIG. 2.

Subsequently, in step S7 of FIG. 5, the crystallographic properties for the target locations 41 are determined based on the first data of the first locations 43 and the second data of the second locations 47.

Referring back to FIG. 3A, according to this embodiment, each of the target locations 41 of the surface 40 has an associated first location, i.e. a first location associated with a respective target location 41, and an associated second location 47, i.e. a second location associated with the respective target location 41. Therefore, the crystallographic properties of the target locations 41 of the entire surface 40 could be determined based on the first data of the first locations 43 or the second data of the second locations 47 or both. One of the advantages of the method is that the crystallographic properties of a particular target location may be determined depending on the quality of the first and second data, the quality of the crystallographic properties determined for each of the first and second data or a combination of the first and second data.

One of these ways is described in the following with reference to FIGS. 4A to 4E. In contrast to the embodiment of the method described above, it is now assumed that a total of three different electron beams of electrons having three different mean kinetic energies are used to detect two-dimensional spatial distributions of electrons for three different sets of locations and three sets of data representing the two-dimensional spatial distribution of electrons are generated for each location of the sets of locations.

One way to determine the crystallographic properties for each location of a set of target locations 41, i.e. a current target location, comprises selecting, as selected data, one of the first data of an associated first location, i.e. a first location associated with the current target location, the second data of an associated second location, i.e. a second location associated with the current target location, and the third data of an associated third location, i. e. a third location associated with the current target location; and determining the crystallographic properties for the current target location based on the selected data.

Figure 4A:
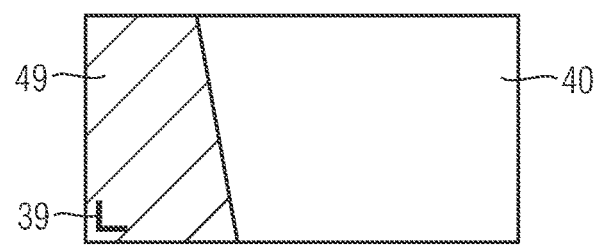
FIG. 4A shows a schematic illustration of a region of the sample of FIG. 3A, wherein the region indicates first locations irradiated by an electron beam of a first mean kinetic energy, wherein first data of the first locations is used for determining crystallographic properties of the sample in the region.

FIG. 4A shows the surface 40 of the sample 3 from a top view as indicated by the x-y-coordinate system referring to the same coordinate system as illustrated in FIG. 3A. For the purpose of orientation, the marker 39 is also shown. A region 49 illustrates those first locations, the first data of which were selected as the selected data to form the basis for determining the crystallographic properties of the target locations of the region 49. That is, the crystallographic properties for the target locations contained in the region 49 are determined based on the first data of the first locations within the regions 49.

Figure 4B:
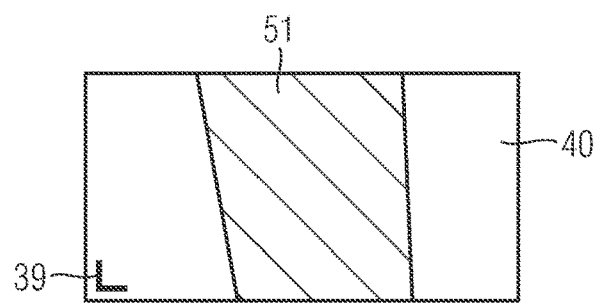
FIG. 4B shows a schematic illustration of a region of the sample of FIG. 3A, wherein the region indicates second locations irradiated by an electron beam of a second mean kinetic energy, wherein second data of the second locations is used for determining crystallographic properties of the sample in the region.

Similarly, FIG. 4B shows the surface 40 of the sample 3 from a top view. A region 51 illustrates those second locations, the second data of which were selected as the selected data to form the basis for determining the crystallographic properties of the target locations of the region 51.

Figure 4C:
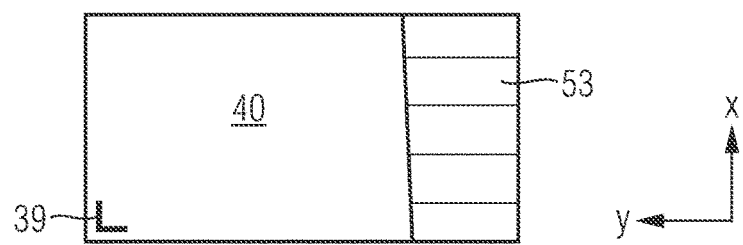
FIG. 4C shows a schematic illustration of a region of the sample of FIG. 3A, wherein the region indicates third locations irradiated by an electron beam of a third mean kinetic energy, wherein third data of the third locations is used for determining crystallographic properties of the sample in the region.

Similarly, FIG. 4C shows the surface 40 of the sample 3 from a top view. A region 53 illustrates those third locations, the third data of which were selected as the selected data to form the basis for determining the crystallographic properties of the target locations of region 53.

Figure 4D:
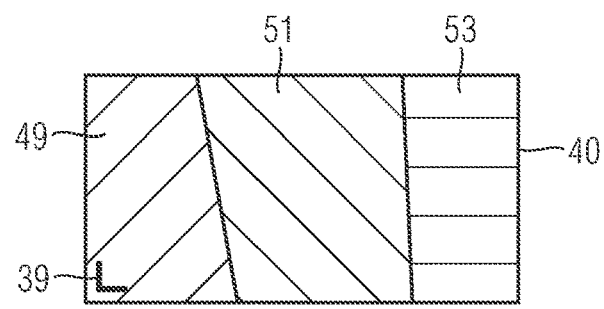
FIG. 4D shows a composite illustration of the regions of FIGS. 4A to 4C.

FIG. 4D shows a composition of the three regions 49, 51 and 53 in a single image. Therefore, all target locations of the surface 40 have associated first, second or third locations based on the data of which the crystallographic properties are determined.

The selecting of data as the selected data may comprise determining a quality parameter such as a contrast value for each of the first, second and third data of the associated first, second and third locations for a current target location, respectively. Therefore, the selected data may be selected by selecting the data having the better quality parameter such as the best contrast among the contrasts of the first, second and third data for a current target location.

The contrast of the data representing a two-dimensional spatial distribution of electrons (see FIG. 2) depends on the mean kinetic energy of the electrons of the electron beam used to generate the respective data. For example, the first mean kinetic energy may be suitable for thin regions of the sample, the second mean kinetic energy may be suitable for a middle region of the sample and the third mean kinetic energy may suitable for a thick region of the sample 3 illustrated in FIG. 3A. This is reflected by the regions 49, 51 and 53 illustrated in FIG. 4D as first data is selected as the basis for determining the crystallographic properties of the target locations of the region 49 where the sample is thin. Similarly, second data determined using a mean kinetic energy suitable for a middle thickness of the sample 3 is selected as the basis for determining the crystallographic properties for target locations of the region 51 where the sample 3 has a middle thickness. Finally, third data determined using the third mean kinetic energy suitable for thick regions of the sample 3 is selected as the basis for determining the crystallographic properties for the target locations of the region 53 where the sample 3 is thick.

Figure 4E:
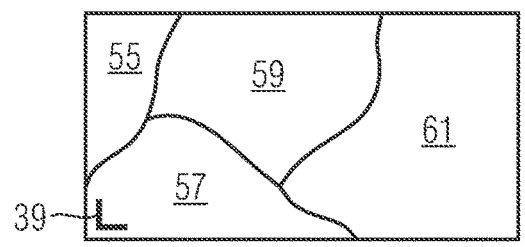
FIG. 4E shows an image representation of a crystallographic property of the sample of FIG. 3A.

FIG. 4E shows an image representation of a crystallographic property such as the orientation of the lattice structure. The image representation comprises four distinct regions 55, 57, 59 and 61 having different values of the crystallographic property. In this example, regarding the crystallographic property as the orientation of a lattice structure, the image representation indicates that the sample 3 comprises four regions of distinct orientations of the lattice structure of the sample. Comparing FIG. 4D and FIG. 4E, it is apparent that the orientation of the lattice structure determined from the first data selected for the target locations of the region 49 may have different values of the orientation. A similar statement holds for the orientation of the lattice structure determined from the second and third data selected for the target locations of the regions 51 and 53, respectively.

According to another embodiment, the determining of the crystallographic properties for each current target location of a set of the target locations comprises combining the first data of a first location associated with the current target location, the second data of a second location associated with the current target location and the third data of a third location associated with the current target location into combined data; and determining the crystallographic properties for the current target location based on the combined data. This is illustrated in the FIGS. 6A to 6D which substantially correspond to FIGS. 4A to 4D of the previously described way for determining the crystallographic properties of target locations.

Figure 6A:
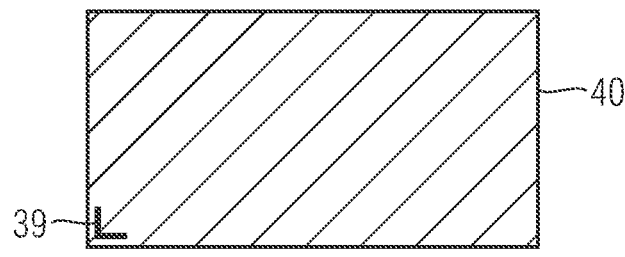
FIG. 6A shows a schematic illustration of a region of the sample of FIG. 3A, wherein the region indicates first locations irradiated by an electron beam of a first mean kinetic energy, wherein first data of the first locations is used for determining crystallographic properties of the sample in the region.
Figure 6B:
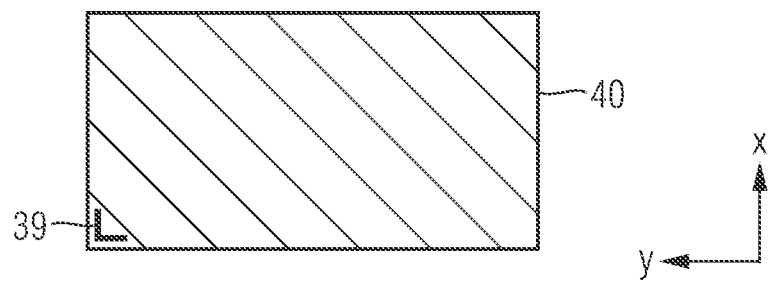
FIG. 6B shows a schematic illustration of a region of the sample of FIG. 3A, wherein the region indicates second locations irradiated by an electron beam of a second mean kinetic energy, wherein second data of the second locations is used for determining crystallographic properties of the sample in the region.
Figure 6C:
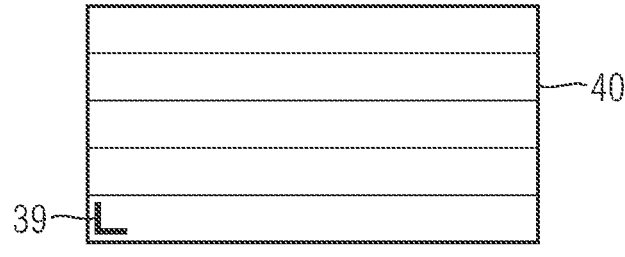
FIG. 6C shows a schematic illustration of a region of the sample of FIG. 3A, wherein the region indicates third locations irradiated by an electron beam of a third mean kinetic energy, wherein third data of the third locations is used for determining crystallographic properties of the sample in the region.
Figure 6D:
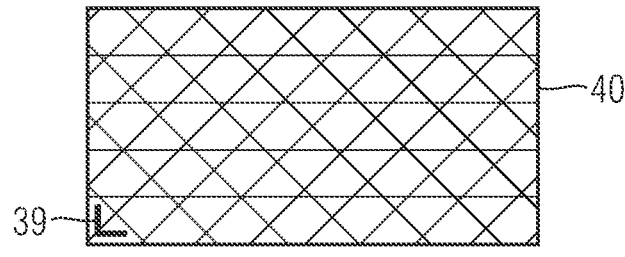
FIG. 6D shows a composite illustration of the regions of FIGS. 6A to 6C.

FIG. 6A shows the region of the surface 40 of the sample 3 illustrated in FIG. 3A containing the first locations, the first data of which are used to determine the crystallographic properties of the target locations. Similarly, FIG. 6B shows the region of the second locations, the second data of which are used to determine the crystallographic properties of the target locations. Similarly, FIG. 6C shows third locations, the third data of which are used to determine the crystallographic properties of the target locations. In fact, as illustrated in FIG. 6D, the first, second and third data of the first, second and third location associated with a particular target location are used, i.e. combined to determine the crystallographic properties of the particular target location. The combining may comprise interpolating the first, second and third data of the first, second and third location associated with the particular location at the particular location. Alternatively or in addition, the combining may comprise averaging and/or superimposing of the first, second and third data of the first, second and third location associated with the current target location.

Figure 7:
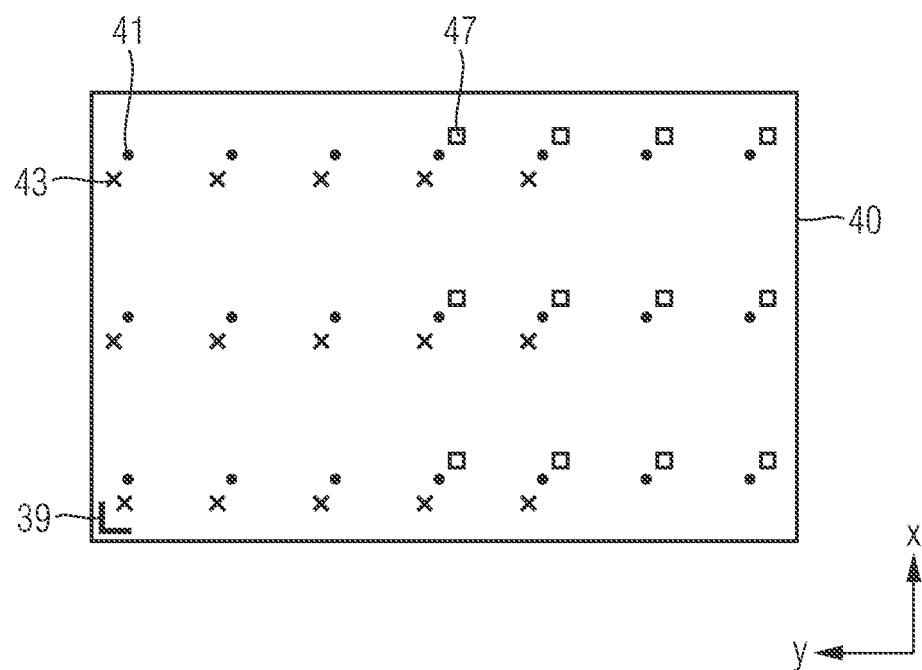
FIG. 7 shows a schematic illustration of target locations, first locations and second locations.

Another embodiment of the method is illustrated with reference to FIG. 7. FIG. 7 shows target locations 41, first locations 43 and second locations 47 on a surface 40 of the sample 3 illustrated in FIG. 3A. In contrast to the embodiment of the method described above with reference to FIG. 3B, in this embodiment, the first locations 43 and the second locations 47 do not cover the entire region defined by the target locations 41. Herein, the first and second locations are determined based on sample information such as a thickness profile of the sample 3. The thickness profile may represent the thickness of the sample 3 in dependence of the coordinates of the local coordinate system of the sample linked to, for example, the marker 39. Based on this thickness profile the first locations may be determined to be located in regions of the sample where the thickness of the sample is less than a predetermined thickness value, whereas the second locations are determined to be located in regions of the sample where the thickness of the sample is greater than the predetermined thickness value. The predetermined thickness value may be a mean thickness of the sample.

By determining the first and second locations based on the sample information, directing the electron beam of electrons having a given mean kinetic energy to regions of the sample for which the given mean kinetic energy is not suitable may be avoided. Therefore, the determining of the crystallographic properties of a sample may be performed in a shorter time.

What is claimed is:

1. A method of determining at least one crystallographic property of a sample, the method comprising:
generating a first electron beam of electrons having a first mean kinetic energy to be irradiated on the sample;
detecting, for each of first locations of a region of the sample, a two-dimensional spatial distribution of electrons transmitting through the sample and being incident onto a detection area while directing the first electron beam onto the first locations;
generating, for each of the first locations, first data representing the two-dimensional spatial distribution;
generating a second electron beam of electrons to be irradiated on the sample, the second electron beam having a second mean kinetic energy different from the first mean kinetic energy;

detecting, for each of second locations of the region of the sample, a two-dimensional spatial distribution of electrons transmitting through the sample and being incident onto the detection area while directing the second electron beam onto the second locations;

generating, for each of the second locations, second data representing the two-dimensional spatial distribution; and generating an image of the sample, wherein:
the image comprises: a) first pixels corresponding to first target locations of the sample; and b) second pixels corresponding to second target locations of the sample;
the second target locations are different from the first target locations;
values at the first pixels represent the at least one crystallographic property and are calculated based on the first data; and
values at the second pixels represent the at least one crystallographic property and are calculated based on the second data.

2. The method according to claim 1, wherein determining the at least one crystallographic property for each current target location of a set of the target locations comprises:
selecting, as selected data, one of the first data of a first location associated with the current target location and the second data of a second location associated with the current target location; and
determining the at least one crystallographic property for the current target location based on the selected data.

3. The method according to claim 2, wherein selecting comprises:
determining a quality parameter for each of the first data of the first location associated with the current target location and the second data of the second location associated with the current target location; and
selecting, as the selected data, the data having the quality parameter that provides a more accurate determination of crystallographic properties.

4. The method according to claim 3, wherein the quality comprises a contrast value.

5. The method according to claim 2, further comprising:
determining the first location associated with the current target location by selecting, among the first locations, the first location having a shortest distance to the current target location; and
determining the second location associated with the current target location by selecting, among the second locations, the second location having a shortest distance to the current target location.

6. The method according to claim 1, wherein determining the at least one crystallographic property for each current target location of a set of the target locations comprises:
combining the first data of a first location associated with the current target location and the second data of a second location associated with the current target location to provide combined data; and
determining the at least one crystallographic property for the current target location based on the combined data.

7. The method according to claim 6, wherein combining the first data and the second comprises:
interpolating the first data of the first location associated with the current target location and the second data of the second location associated with the current target location; and/or averaging the first data of the first location associated with the current target location and the second data of the second location associated with the current target location.

8. The method according to claim 1, wherein determining the at least one crystallographic property for each current target location of a set of the target locations comprises:
determining the at least one crystallographic property for a first location associated with the current target location based on the first data;
determining the at least one crystallographic property for a second location associated with the current target location based on the second data; and
selecting, as the at least one crystallographic property for the current target location, one of the at least one crystallographic property determined for the first and second locations associated with the current target location.

9. The method according to claim 8, wherein selecting comprises:
determining a quality parameter for each of the at least one crystallographic property determined for the first and second locations associated with the current target location; and
selecting, as the at least one crystallographic property of the current target location, the at least one crystallographic property having the quality parameter that provides a more accurate determination of crystallographic properties.

10. The method according to claim 9, wherein the quality parameter comprises a deviation from a predetermined expected value.

11. The method according to claim 1, further comprising:
generating an image representation of the at least one crystallographic property of the target locations; and/or
determining the first and second locations based on sample information, in particular a thickness profile of the sample.

12. The method according to claim 1, wherein determining the at least one crystallographic property comprises identifying and indexing of Kikuchi bands.

13. The method according to claim 1, wherein at least one of the following holds:
the detected electrons are electrons transmitted through the sample; and
detecting comprises generating detection signals representing a two-dimensional distribution of intensities of electrons incident onto the detection area.

14. The method according to claim 1, further comprising:
recording a first image of the sample when using the first electron beam, recording a second image of the sample when using the second electron beam; and
aligning the first and second locations based on the first and second images.

15. The method according to claim 1, wherein the first and second mean kinetic energies differ by at least one of:
1 keV, 2 keV, 5 keV and 10 keV; and
1%, 2%, 5% and 10% of a mean value of the first mean kinetic energy and the second mean kinetic energy.

16. The method according claim 1, wherein each of the first and second mean kinetic energies is in a range of 10 keV to 30 keV.

17. The method according to claim 1, according to claim 1 wherein generating the first and second electron beams comprises selecting the first and second mean kinetic energies based on:

sample information, in particular a thickness profile of the sample; or two-dimensional spatial distributions of electrons emerging from the sample and being incident onto the detection area.

18. The method according to claim 1, wherein directing the first electron beam onto the first locations and directing the second electron beam onto the second locations comprises: a) deflecting the first and second electron beams; or b) displacing the sample relative to the first and second electron beams.

19. An electron beam microscope, comprising:
an electron beam column;
a two-dimensional spatially resolving electron detector; and
a controller, comprising:
a processing device; and
a machine-readable hardware storage device comprising instructions that are executable by the processing device to perform operations comprising the method according to claim 1.

20. A method of determining at least one crystallographic property of a sample, comprising:
detecting, for each of first locations of a region of the sample, a two-dimensional spatial distribution of electrons transmitting through the sample and being incident onto a detection area while directing a first electron beam onto the first locations;
generating, for each of the first locations, first data representing the two-dimensional spatial distribution;
detecting, for each of second locations of the region of the sample, a two-dimensional spatial distribution of electrons transmitting through the sample and being incident onto the detection area while directing a second electron beam onto the second locations;
generating, for each of the second locations, second data representing the two-dimensional spatial distribution; and
generating an image of the sample,
wherein:
the image comprises: a) first pixels corresponding to first target locations of the sample; and b) second pixels corresponding to second target locations of the sample;
the second target locations are different from the first target locations;
values at the first pixels represent the at least one crystallographic property and are calculated based on the first data; and
values at the second pixels represent the at least one crystallographic property and are calculated based on the second data, and
wherein the first electron beam of electrons has a first mean kinetic energy when irradiated on the sample, and the second electron beam of electrons has a second mean kinetic energy when irradiated on the sample which is different from the first mean kinetic energy.

21. An electron beam microscope, comprising:
an electron beam column;
a two-dimensional spatially resolving electron detector; and
a controller, comprising:
a processing device; and
a machine-readable hardware storage device comprising instructions that are executable by the processing device to perform operations comprising the method according to claim 20.

22. The method according to claim 1, wherein the at least one crystallographic property are at least one of an orientation of a lattice structure, a lattice type and lattice parameters.

* * * * *

UNITED STATES PATENT AND TRADEMARK OFFICE
CERTIFICATE OF CORRECTION

PATENT NO. : 10,319,560 B2
APPLICATION NO. : 15/209988
DATED : June 11, 2019
INVENTOR(S) : Giuseppe Pavia Page 1 of 1

It is certified that error appears in the above-identified patent and that said Letters Patent is hereby corrected as shown below:

In the Claims

Column 16, Line 61, Claim 16, after "according" insert -- to --;

Column 16, Lines 64-65, Claim 17, after "claim 1," delete "according to claim 1".

Signed and Sealed this
Fifth Day of May, 2020

Andrei Iancu
*Director of the United States Patent and Trademark Office*